United States Patent
Konishi et al.

(10) Patent No.: US 10,533,282 B2
(45) Date of Patent: Jan. 14, 2020

(54) METHOD FOR RECOVERING PULP FIBERS FROM USED ABSORBENT ARTICLE

(71) Applicant: UNICHARM CORPORATION, Ehime (JP)

(72) Inventors: Takayoshi Konishi, Kagawa (JP); Toshio Hiraoka, Kagawa (JP); Koichi Yamaki, Kagawa (JP); Noritomo Kameda, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 16/322,111

(22) PCT Filed: Jun. 9, 2017

(86) PCT No.: PCT/JP2017/021540
§ 371 (c)(1),
(2) Date: Jan. 31, 2019

(87) PCT Pub. No.: WO2018/025500
PCT Pub. Date: Feb. 8, 2018

(65) Prior Publication Data
US 2019/0338463 A1 Nov. 7, 2019

(30) Foreign Application Priority Data

Aug. 5, 2016 (JP) .................. 2016-154939
Apr. 6, 2017 (JP) .................. 2017-076088

(51) Int. Cl.
*D21C 5/02* (2006.01)
*A61L 2/18* (2006.01)
(Continued)

(52) U.S. Cl.
CPC .............. *D21C 5/022* (2013.01); *B09B 3/00* (2013.01); *B29B 17/02* (2013.01); *C08J 11/26* (2013.01);
(Continued)

(58) Field of Classification Search
None
See application file for complete search history.

(56) References Cited

U.S. PATENT DOCUMENTS
2017/0107667 A1   4/2017 Konishi et al.

FOREIGN PATENT DOCUMENTS
EP   3238840 A1   11/2017
JP   H4-317785 A   11/1992
(Continued)

*Primary Examiner* — Dennis R Cordray
(74) *Attorney, Agent, or Firm* — Hauptman Ham, LLP

(57) ABSTRACT

A method is provided which, by a simple process, separates and recovers pulp fibers from a used absorbent article that contains pulp fibers and a superabsorbent polymer. A used absorbent article is treated with an aqueous solution that contains greater than or equal to 0.05 mass % of at least one kind of terpene selected from the group comprising terpene hydrocarbons, terpene aldehydes, and terpene ketones and that contains a deactivating agent that can deactivate the superabsorbent polymer; the superabsorbent polymer is deactivated, the adhesive that bonds together the constituent materials of the absorbent article is dissolved with the terpene to decompose the absorbent article, the pulp fibers are discharged to outside of the absorbent article, and the pulp fibers are separated from the absorbent article and recovered.

13 Claims, 2 Drawing Sheets

(51) Int. Cl.
*B09B 3/00* (2006.01)
*C08J 11/16* (2006.01)
*A61L 12/00* (2006.01)
*D21B 1/02* (2006.01)
*D21H 11/14* (2006.01)
*D21C 11/00* (2006.01)
*B29B 17/02* (2006.01)
*C08J 11/26* (2006.01)
*B29L 31/48* (2006.01)
*A61L 11/00* (2006.01)

(52) U.S. Cl.
CPC ............. *D21B 1/021* (2013.01); *D21B 1/026* (2013.01); *D21C 11/0007* (2013.01); *D21H 11/14* (2013.01); *A61L 2/183* (2013.01); *A61L 11/00* (2013.01); *B29B 2017/0293* (2013.01); *B29L 2031/4878* (2013.01)

(56) References Cited

FOREIGN PATENT DOCUMENTS

| | | | |
|---|---|---|---|
| JP | 2003-39023 | A | 2/2003 |
| JP | 2003-225645 | A | 8/2003 |
| JP | 2007-159604 | A | 6/2007 |
| JP | 2010-84031 | A | 4/2010 |
| JP | 2012-66156 | A | 4/2012 |
| JP | 2014-217835 | A | 11/2014 |
| JP | 2016-123973 | A | 7/2016 |
| WO | 2007/070269 | A1 | 6/2007 |
| WO | 2015/190140 | A1 | 12/2015 |

FIG. 1
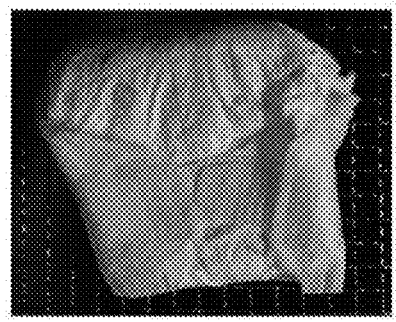
FIG. 2A   FIG. 2B   FIG. 2C
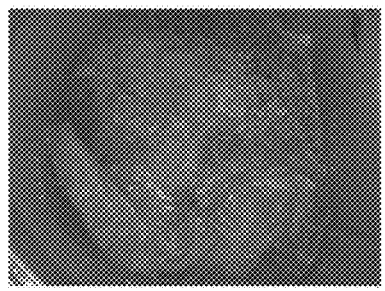  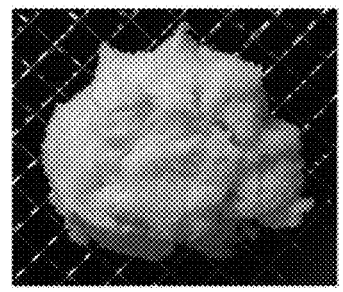
FIG. 3A   FIG. 3B   FIG. 3C
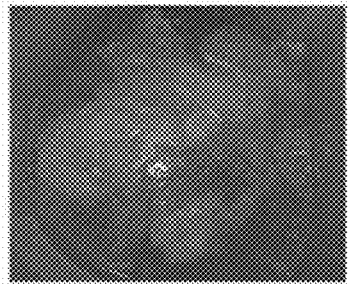 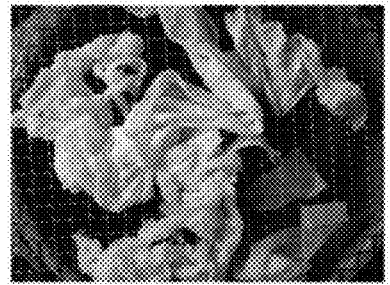 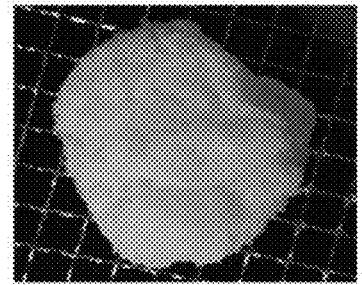

METHOD FOR RECOVERING PULP FIBERS FROM USED ABSORBENT ARTICLE

RELATED APPLICATIONS

The present application is a National Phase of International Application Number PCT/JP2017/021540, filed on Jun. 9, 2017, and claims priority of Japanese Application Number 2017-076088, filed on Apr. 6, 2017 and Japanese Application Number 2016-154939, filed on Aug. 5, 2016.

FIELD

The present invention relates to a method for recovering pulp fibers from a used absorbent article.

BACKGROUND

It has been attempted to recycle used absorbent articles such as disposable paper diapers. For recycling of used absorbent articles, it is common to disintegrate the used absorbent articles in water, separating them into the constituent components of the absorbent articles, which are then recovered. However, the superabsorbent polymers that are included in absorbent articles absorb moisture and increase in mass, while also gelling and losing their flow property, causing the throughput capacity of the treatment apparatus to be reduced.

In this regard, Japanese Unexamined Patent Publication No. 2010-84031 proposes a method of treating used paper diapers wherein lime, a hypochlorite and used paper diapers are loaded into a treatment tank and stirred for a prescribed period while supplying water in the minimum amount necessary for stirring in the treatment tank, the liquid in the treatment tank is discharged out of the treatment tank while dewatering, and the discharged waste water is recovered, subjected to water quality treatment and discarded.

CITATION LIST

Patent Literature

[PTL 1] Japanese Unexamined Patent Publication No. 2010-84031

SUMMARY

Technical Problem

In the method of Japanese Unexamined Patent Publication No. 2010-84031, however, even after the lime, hypochlorite and used paper diapers have been loaded into the treatment tank and stirred for the prescribed period of time while supplying water in the minimum amount necessary to allow stirring in the treatment tank, the used paper diapers essentially maintain their original form with the front sheet and back sheet attached, and therefore the pulp fibers cannot be easily separated and recovered from the used paper diapers.

Solution to Problem

The present inventors have focused on this problem of the prior art, and have completed this invention after finding that when used absorbent articles are treated with an aqueous solution containing an inactivating agent that can inactivate superabsorbent polymers, addition of a terpene to the aqueous solution allows ordinary temperature-dissolution of the hot-melt adhesive that bonds together the constituent materials of the paper diapers or other absorbent articles, decomposition of the absorbent articles into their constituent elements, and dispersion of the pulp fibers in the used paper diapers into the treatment tank, thus facilitating separation and recovery of the pulp fibers from the absorbent articles.

Specifically, the present invention is a method for recovering pulp fibers from a used absorbent article that contains pulp fibers and a superabsorbent polymer, wherein the method includes a step of treating the used absorbent article with an aqueous solution containing at least one kind of terpene selected from the group consisting of terpene hydrocarbons, terpene aldehydes and terpene ketones at 0.05 mass % or greater, and also containing an inactivating agent that can inactivate the superabsorbent polymer, for inactivation of the superabsorbent polymer.

The invention encompasses the following aspects.

[1] A method of recovering pulp fibers from a used absorbent article that contains pulp fibers and a superabsorbent polymer, wherein the method includes a step of treating the used absorbent article with an aqueous solution containing at least one kind of terpene selected from the group consisting of terpene hydrocarbons, terpene aldehydes and terpene ketones at 0.05 mass % or greater, and also containing an inactivating agent that can inactivate the superabsorbent polymer, to inactivate the superabsorbent polymer.

[2] The method according to [1], which further includes a step of separating the pulp fibers and the inactivated superabsorbent polymer from the used absorbent article that has been treated with the aqueous solution.

[3] The method according to [2], which further includes a step of treating a mixture comprising separated pulp fibers and an inactivated superabsorbent polymer with an oxidizing agent to decompose, reduce in molecular weight and solubilize the inactivated superabsorbent polymer.

[4] The method according to [3], which further includes a step of separating the pulp fibers from the mixture that has been treated with the oxidizing agent.

[5] The method according to any one of [1] to [4], wherein the aqueous solution containing the inactivating agent that can inactivate the superabsorbent polymer is an organic acid aqueous solution with a pH of no higher than 2.5.

[6] The method according to [5], wherein the organic acid is citric acid.

[7] The method according to [6], wherein a citric acid concentration in the organic acid aqueous solution is 2 mass % or greater.

[8] The method according to any one of [1] to [7], wherein the terpene is a terpene hydrocarbon.

[9] The method according to [8], which the terpene hydrocarbon is limonene.

[10] The method according to any one of [1] to [9], wherein a terpene concentration in the aqueous solution is 0.05 to 1.0 mass %.

[11] The method according to any one of [2] to [10], wherein the used absorbent article includes a material composed of a thermoplastic resin, and the method further includes a step of drying a residue obtained from separating the pulp fibers and the inactivated superabsorbent polymer from the used absorbent article, and separating the material composed of a thermoplastic resin from the dried residue.

[12] The method according to any one of [2] to [10], wherein the used absorbent article includes a thermoplastic resin film, and the method further includes a step of drying a residue obtained from separating the pulp fibers and the inactivated superabsorbent polymer from the used absorbent article, and separating the thermoplastic resin film from the dried residue.

[13] The method according to any one of [1] to [12], wherein the absorbent article is at least one type selected from the group consisting of paper diapers, urine-absorbing pads, bed sheets, sanitary napkins and pet sheets.

Advantageous Effects of Invention

According to the method of the invention it is possible to separate and recover pulp fibers from a used absorbent article that contains pulp fibers and a superabsorbent polymer, by a simple process.

BRIEF DESCRIPTION OF DRAWINGS

FIG. 1 is a photograph of the paper diaper used in Examples 3 to 7, before treatment.

FIG. 2A shows a photograph of the washing tank interior after the treatment of Example 3, FIG. 2B shows a photograph of the recovered nonwoven fabric, film, etc. after treatment, and FIG. 2C shows a photograph of the recovered pulp fibers and inactivated superabsorbent polymer after treatment.

FIG. 3A shows a photograph of the washing tank interior after the treatment of Example 4, FIG. 3B shows a photograph of the recovered nonwoven fabric, film, etc. after treatment, and FIG. 3C shows a photograph of the recovered pulp fibers and inactivated superabsorbent polymer after treatment.

DESCRIPTION OF EMBODIMENTS

Figure 4A:
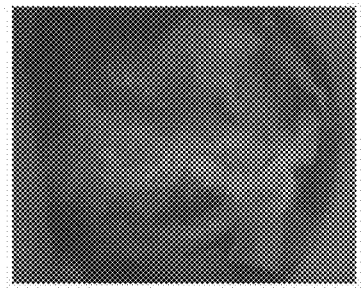
FIG. 4A shows a photograph of the washing tank interior after the treatment of Example 5.

The invention is a method for recovering pulp fibers from a used absorbent article that contains pulp fibers and a superabsorbent polymer.

The absorbent article is not particularly restricted so long as it contains pulp fibers and a superabsorbent polymer, and examples include paper diapers, urine-absorbing pads, bed sheets, sanitary napkins and pet sheets. Such absorbent articles are usually composed of constituent materials such as pulp fibers, a superabsorbent polymer, a nonwoven fabric, a thermoplastic resin film and a hot-melt adhesive.

There are no particular restrictions on the pulp fibers, and examples include fluffy pulp fibers and chemical pulp fibers.

A superabsorbent polymer, also known as SAP, has a three-dimensional network structure with an appropriately crosslinked water-soluble polymer, and therefore absorbs a few hundred to a few thousand times its weight in water while being essentially water-insoluble and preventing absorbed water from emerging even with some degree of pressure application, and examples thereof include starch-based, acrylic acid-based and amino acid-based particulate or fibrous polymers.

The method of the invention includes a step of treating the used absorbent article with an aqueous solution containing at least one kind of terpene selected from the group consisting of terpene hydrocarbons, terpene aldehydes and terpene ketones at 0.05 mass % or greater, and also containing an inactivating agent that can inactivate the superabsorbent polymer, to inactivate the superabsorbent polymer (this will hereunder be referred to simply as "inactivating step"). In this step, the superabsorbent polymer is inactivated while the terpene dissolves the hot-melt adhesive that bonds the constituent materials of the absorbent article, and the absorbent article is broken up into its constituent materials by the force of stirring and washing, causing the pulp fibers in the absorbent article to be dispersed in the treatment tank. In addition, terpene has a high washing effect for contaminating oils, and in addition to its dissolving effect for the hot-melt adhesive, it also decomposes and removes printing inks that may be present in printed matter on a leakproof film as one of the constituent materials of the absorbent article, and therefore also allows recovery of printed leakproof films as highly pure plastic materials.

The inactivating agent that can inactivate superabsorbent polymers may be, but is not limited to, organic acids, lime, calcium chloride, magnesium sulfate, magnesium chloride, aluminum sulfate and aluminum chloride, among which organic acids are preferred.

An organic acid is unlikely to damage the pulp fibers, and therefore using an organic acid allows recovery of pulp fibers with low damage, i.e. pulp fibers with a high water absorption factor and high water retention factor. When an organic acid is used as the inactivating agent, the pH of the organic acid aqueous solution is no higher than 2.5. In other words, the aqueous solution containing the inactivating agent that can inactivate the superabsorbent polymer is an organic acid aqueous solution having a pH of preferably no higher than 2.5.

Organic acids include citric acid, tartaric acid, glycolic acid, malic acid, succinic acid, acetic acid and ascorbic acid, with citric acid being particularly preferred. The chelating effect of citric acid traps metal ions and the like present in excreta, allowing their removal, and the washing effect of citric acid can potentially provide a high fouling component-removal effect.

The pH of the organic acid aqueous solution is no higher than 2.5, preferably 1.3 to 2.4 and more preferably 1.5 to 2.1. If the pH is too high, it may not be possible to sufficiently lower the water-absorbing capacity of the superabsorbent polymer. The sterilizing ability may also be reduced, potentially making sterilization impossible. If the pH is too low, the risk of corrosion of the equipment will increase, lowering its service life, and large amounts of alkaline chemicals may be necessary for neutralizing treatment during waste water treatment.

The pH varies depending on the water temperature, but the pH for the purpose of the invention is the pH measured at an aqueous solution temperature of 20° C.

The organic acid concentration of the organic acid aqueous solution is not restricted so long as the pH of the organic acid aqueous solution is no higher than 2.5, but when the organic acid is citric acid, the citric acid concentration is preferably 2 mass % or greater, more preferably 2.0 to 4.0 mass % and even more preferably 2.0 to 3.0 mass %.

The aqueous solution containing the inactivating agent that can inactivate superabsorbent polymers contains at least one kind of terpene selected from the group consisting of terpene hydrocarbons, terpene aldehydes and terpene ketones.

Terpene hydrocarbons include myrcene, limonene, pinene, camphor, sabinene, phellandrene, paracymene, ocimene, terpinene, carene, zingiberene, caryophyllene, bisabolene and cedrene, among which limonene, pinene, terpinene and carene are preferred.

Terpene aldehydes include citronellal, citral, cyclocitral, safranal, phellandral, perylaldehyde, geranial and neral, among which citral is preferred.

Terpene ketones include camphor and thujone.

Terpene hydrocarbons are preferred terpenes, with limonene being a particularly preferred terpene. Limonenes are of three types: d-limonene, l-limonene and dipentene (dl-limonene), and all of them are suitable for use.

A single type of terpene may be used, or two or more may be used in combination.

The terpene concentration in the aqueous solution is 0.05 mass % or greater, preferably 0.05 to 1.0 mass % and more preferably 0.075 to 0.5 mass %. If the terpene concentration is too low, it may not be possible to efficiently disintegrate the paper diaper into its constituent materials. Cost may increase if the terpene concentration is too high.

The aqueous solution may also contain a detergent or the like.

The treatment temperature, i.e. the aqueous solution temperature, is not particularly restricted, and it may be heated or at room temperature, such as at 15 to 30° C.

The treatment time is not limited so long as the superabsorbent polymer can be inactivated and the used absorbent article can be disintegrated into its constituent materials, but it is preferably 5 to 60 minutes and more preferably 10 to 30 minutes.

The amount of aqueous solution is not limited so long as the superabsorbent polymer can be inactivated and the used absorbent article can be disintegrated into its constituent materials, but it is preferably 300 to 3000 parts by mass, more preferably 500 to 2500 parts by mass and even more preferably 1000 to 2000 parts by mass with respect to 100 parts by mass of the used absorbent article.

The method of treating the used absorbent article with the aqueous solution is not particularly restricted, and for example, a prescribed amount of the used absorbent article is loaded into washing equipment and an aqueous solution containing a terpene at 0.05 mass % or greater and containing an inactivating agent that can inactivate the superabsorbent polymer is loaded in, with stirring if necessary. A detergent or the like may also be added to the aqueous solution if necessary.

The method of the invention may further include a step of separating the pulp fibers and the inactivated superabsorbent polymer from the used absorbent article that has been treated with the aqueous solution (hereunder also referred to simply as "separating step"). The method of separating the pulp fibers and the inactivated superabsorbent polymer is not limited, and for example, the mixture produced by the inactivating step may be discharged while being passed through a screen having preferably a mesh opening of 5 to 100 mm and more preferably a mesh opening of 10 to 80 mm, to separate the pulp fibers and the inactivated superabsorbent polymer into the drainage while leaving the other large-sized matter such as the nonwoven fabric and thermoplastic resin film on the screen.

The method of the invention may further include a step of treating the mixture comprising separated pulp fibers and an inactivated superabsorbent polymer with an oxidizing agent to decompose, reduce in molecular weight and solubilize the inactivated superabsorbent polymer (hereunder also referred to simply as "oxidizing agent treatment step"). By treating the mixture of the pulp fibers and the inactivated superabsorbent polymer with an oxidizing agent, it is possible to oxidatively decompose, reduce in molecular weight and solubilize the inactivated superabsorbent polymer while carrying out secondary sterilization, bleaching and deodorization of the pulp fibers. The decomposed, molecular weight-reduced and solubilized state of the superabsorbent polymer means a state in which it passes through a 2 mm screen. In other words, in this step, the superabsorbent polymer is decomposed until it passes through a screen with a mesh opening of 2 mm.

The oxidizing agent is not limited so long as it can decompose, reduce in molecular weight and solubilize the inactivated superabsorbent polymer, and examples include chlorine dioxide, ozone and sodium hypochlorite. Ozone is preferred among these from the viewpoint of height decomposing power and effect on the environment.

The method of treatment with the oxidizing agent is not limited so long as it can decompose, reduce in molecular weight and solubilize the inactivated superabsorbent polymer, and for example, the oxidizing agent may be added to the drainage containing the pulp fibers and inactivated superabsorbent polymer, which is obtained after separation through the screen in the separating step. Alternatively, the drainage may be further passed through a fine screen that does not allow passage of the pulp fibers and inactivated superabsorbent polymer, thus separating the pulp fibers and inactivated superabsorbent polymer from the drainage, and the separated pulp fibers and inactivated superabsorbent polymer may be added to an aqueous solution of the oxidizing agent.

When ozone is used as the oxidizing agent, the oxidizing agent treatment may be carried out by contacting the mixture containing the pulp fibers and inactivated superabsorbent polymer with the ozone, or more specifically, the ozone may be blown into the drainage containing the pulp fibers and inactivated superabsorbent polymer. Ozone can be generated using, for example, an ozone water generator (such as an ED-OWX-2 ozone water exposure tester by EcoDesign, Inc. or an OS-25V ozone generator by Mitsubishi Electric Corp.).

When ozone is blown into drainage containing the pulp fibers and inactivated superabsorbent polymer, the ozone concentration in the drainage is not particularly restricted so long as it is a concentration allowing decomposition of the superabsorbent polymer, and it is preferably 1 to 50 ppm by mass, more preferably 2 to 40 ppm by mass and even more preferably 3 to 30 ppm by mass. If the concentration is too low it may not be possible to completely solubilize the superabsorbent polymer, potentially leading to residue of the superabsorbent polymer in the recovered pulp fibers. If the concentration is too high, conversely, the oxidizing power will increase, potentially damaging the pulp fiber and possibly causing problems in terms of safety.

The ozone treatment time is not particularly restricted so long as it is a time allowing the superabsorbent polymer to be decomposed. The treatment time may be short if the ozone concentration is high, but it must be a longer time if the ozone concentration is low.

The product of the ozone concentration (ppm) and the treatment time (min) (hereunder also referred to as "CT value") is preferably 100 to 6000 ppm·min, more preferably 200 to 4800 ppm. min and even more preferably 300 to 3600 ppm min. If the CT value is too low it may not be possible to completely solubilize the superabsorbent polymer, potentially leading to residue of the superabsorbent polymer in the recovered pulp fibers. Conversely, an excessively large CT value may result in damage to the pulp fibers, reduced safety and increased manufacturing cost.

The treatment time will depend on the ozone concentration, as explained above, but it is preferably 20 to 120 minutes, more preferably 30 to 100 minutes and even more preferably 40 to 80 minutes.

The temperature during ozone treatment is not particularly restricted so long as it is a temperature allowing the superabsorbent polymer to be decomposed. When ozone is to be blown into drainage containing the pulp fibers and inactivated superabsorbent polymer, the drainage may be heated or at room temperature.

In the oxidizing agent treatment step, the superabsorbent polymer undergoes oxidative decomposition by the oxidizing agent and the three-dimensional network structure of the superabsorbent polymer collapses, the superabsorbent polymer losing its water retention and becoming reduced in molecular weight and solubilized.

When ozone is to be blown into drainage containing the pulp fibers and inactivated superabsorbent polymer, the drainage is preferably acidic. More preferably, the pH of the drainage is no higher than 2.5, and even more preferably 1.5 to 2.4. Treatment in an acidic state can improve the superabsorbent polymer decomposing and removal effect of the ozone, allowing the superabsorbent polymer to be decomposed in a shorter time.

When chlorine dioxide is used as the oxidizing agent, the oxidizing agent treatment may be carried out by contacting the mixture containing the pulp fibers and inactivated superabsorbent polymer with the chlorine dioxide, or more specifically, the chlorine dioxide may be blown into the drainage containing the pulp fibers and inactivated superabsorbent polymer. The chlorine dioxide used may be a commercially available product.

When chlorine dioxide is to be blown into drainage containing the pulp fibers and inactivated superabsorbent polymer, the chlorine dioxide concentration in the drainage is not particularly restricted so long as it is a concentration allowing decomposition of the superabsorbent polymer, and it is preferably 150 to 1100 ppm by mass, more preferably 200 to 1000 ppm by mass and even more preferably 300 to 900 ppm by mass. If the concentration is too low it may not be possible to completely solubilize the superabsorbent polymer, potentially leading to residue of the superabsorbent polymer in the recovered pulp fibers. If the concentration is too high, conversely, the oxidizing power will increase, potentially damaging the pulp fibers and possibly causing problems in terms of safety.

The treatment time is the same as for ozone treatment.

When sodium hypochlorite is used as the oxidizing agent, the oxidizing agent treatment may be carried out by contacting the mixture containing the pulp fibers and inactivated superabsorbent polymer with the sodium hypochlorite, or more specifically, the sodium hypochlorite may be added to the drainage containing the pulp fibers and inactivated superabsorbent polymer, or the pulp fibers and inactivated superabsorbent polymer separated from the drainage by a screen may be immersed in an aqueous solution of the sodium hypochlorite. The sodium hypochlorite used may be a commercially available product.

When sodium hypochlorite is to be added to drainage containing the pulp fibers and inactivated superabsorbent polymer, or when the pulp fibers and inactivated superabsorbent polymer are to be immersed in an aqueous solution of the sodium hypochlorite, the sodium hypochlorite concentration in the drainage or in the aqueous solution of the sodium hypochlorite is not particularly restricted so long as it is a concentration allowing decomposition of the superabsorbent polymer, but it is preferably 0.5 to 2 mass % and more preferably 0.75 to 1.5 mass %. If the concentration is too low it may not be possible to completely solubilize the superabsorbent polymer, potentially leading to residue of the superabsorbent polymer in the recovered pulp fibers. It may also be impossible to completely sterilize out spore-forming *Bacillus subtilis*. If the concentration is too high, conversely, the oxidizing power will increase, potentially damaging the pulp fibers and possibly causing problems in terms of safety.

The treatment time is the same as for ozone treatment.

The method of the invention may further include a step of separating the pulp fibers from a mixture treated by an oxidizing agent (hereunder also referred to simply as "pulp fiber separating step"). The method of separating the pulp fibers is not particularly restricted, and for example, the pulp fibers may be separated by passing the mixture that has been treated by the oxidizing agent through a screen with a mesh opening of 0.15 to 2 mm. If the mixture that has been treated by the oxidizing agent, and more specifically the drainage containing the pulp fibers and decomposed superabsorbent polymer, is passed through a screen with a mesh opening of 0.15 to 2 mm, the drainage containing the decomposed superabsorbent polymer will pass through the screen while the pulp fibers will remain on the screen.

The separated pulp fibers may be dewatered, dried and recovered as necessary.

The drying temperature for drying is preferably 105 to 210° C., more preferably 110 to 190° C. and even more preferably 120 to 180° C. The drying time will depend on the drying temperature, but it is preferably 10 to 120 minutes, more preferably 15 to 100 minutes and even more preferably 20 to 90 minutes.

When the used absorbent article includes a material composed of a thermoplastic resin, the method of the invention may further include a step of drying the residue obtained from separating the pulp fibers and the inactivated superabsorbent polymer from the used absorbent article, and separating the material composed of a thermoplastic resin from the dried residue (hereunder also referred to simply as "thermoplastic resin material separating step"). Secondary sterilization of the residue can be accomplished by drying the residue. The "material composed of a thermoplastic resin" referred to here is a nonwoven fabric or film composed of a thermoplastic resin such as polyethylene, polypropylene or polyester. The separated material composed of a thermoplastic resin may be converted to RPF (conversion to solid fuel). When an oxidizing agent treatment step is not provided, or when an oxidizing agent treatment step is provided but ozone is used as the oxidizing agent, no chlorine-based agents will be present during the RPF conversion step, and therefore high-quality RPF can be produced without damaging the furnace.

When the used absorbent article includes a thermoplastic resin film, the method of the invention may further include a step of drying the residue obtained from separating the pulp fibers and the inactivated superabsorbent polymer from the used absorbent article, and separating the thermoplastic resin film from the dried residue (hereunder also referred to simply as "film separating step"). Secondary sterilization of the residue can be accomplished by drying the residue. The separated thermoplastic resin film may be pelletized for regeneration as a plastic bag or film.

With the present invention it is possible for the hot-melt adhesive that is bonding each of the materials of the absorbent article together to be dissolved at ordinary temperature, by adding a terpene at a concentration of 0.05 mass % or greater to an organic acid aqueous solution, as an aqueous solution containing an inactivating agent that can inactivate superabsorbent polymers, thereby facilitating easy and clean dispersed separation of the absorbent article, and it is thus possible to separate the pulp fibers and superabsorbent polymer from the absorbent article and to separate and recover the nonwoven fabric and film while retaining their material forms. That is, it is possible to easily recover pulp fibers, films and nonwoven fabrics without crushing the paper diapers and without a complex separating step. When limonene is used as the terpene, a secondary effect of the limonene provides a refreshing, citrus-like odor and can therefore mask odors from excreta to some extent, reducing the burden of odors on operating personnel and the effect of odors on the surroundings. Since limonene is a monoterpene and has a structure similar to styrene, it can dissolve styrene-based hot-melt adhesives that are commonly used in absorbent articles such as paper diapers. Since washing treatment of absorbent articles such as paper diapers is possible at ordinary temperature, energy costs can be reduced and diffusion of odors can be minimized. Terpene has a high washing effect for contaminating oils, and in addition to its dissolving effect for the hot-melt adhesive, it can also decompose and remove printing inks that may be present in printed matter on leakproof films, and therefore also allows recovery of printed leakproof films as highly pure plastic materials.

When lime is used for treatment of used absorbent articles as described in Japanese Unexamined Patent Publication No. 2010-84031, the lime creates an environment with a high pH (12.4) inside the treatment tank, and the cellulose swells causing the pulp fibers to undergo alkali cellulose conversion and degradation, whereas the pulp fibers are less likely to undergo degradation when using an organic acid aqueous solution with a pH of no higher than 2.5 for inactivation of the superabsorbent polymer. When citric acid is used as the organic acid, the chelating effect and washing power of the citric acid can potentially provide an effect of removing fouling components from excreta. A sterilizing effect and a deodorant effect against alkaline odors may also be expected.

By decomposing and removing the inactivated superabsorbent polymer with an oxidizing agent, it is possible to prevent contamination of the recovered pulp fibers or drastic increase in sludge due to water absorption by the superabsorbent polymer. By adjusting the type and concentration of oxidizing agent used, it is possible to simultaneously carry out oxidative decomposition and sterilization of the inactivate water-absorbent polymer. When an oxidizing agent treatment step is not provided, or when an oxidizing agent treatment step is provided but ozone is used as the oxidizing agent, since absolutely no chlorine-based agents are used in the step of recovering the nonwoven fabric and film materials, high-quality RPF can be produced, that is unlikely to damage the combustion furnace. If the film material is separated and recovered, it can be reused as a raw material for a bag or film. Since no salts are used during the treatment steps, there is no residue in the recovered pulp and high quality pulp with a low ash content can be recovered.

EXAMPLES

The present invention will now be explained in more specific detail through the following examples, with the understanding that the invention is in no way limited to the examples.

Example 1

After immersing 100 g of standard compost (YK-8, product of Yawata Corp.) in 1 L of ion-exchanged water and stirring for 5 minutes, the mixture was allowed to stand for 30 minutes and 240 mL of the supernatant solution was sampled, to prepare artificial sewage. The prepared artificial sewage was subjected to ATP inspection using a Lumitester PD-30 by Kikkoman Corp. as the measuring instrument, resulting in an ATP value of 13126.

Commercially available paper diapers (Moony® M size by Unicharm Corp.) were used to absorb 240 mL of the previously prepared artificial sewage, and then one paper diaper was loaded into a washing tank of a dual-tank miniature washing machine ("HareBare" AST-01 by Alumis Co.), after which 10 L of an aqueous solution (pH 2.1), comprising citric acid (product of Fuso Chemical Co., Ltd.) dissolved at a concentration of 2.0 mass % and d-limonene (Special Grade by Nacalai Tesque, Inc.) dissolved at a concentration of 0.05 mass % in water at a temperature of 20° C., was loaded in and washing was carried out for 15 minutes. After washing was complete, the front sheet and back sheet of the diaper were detached, causing the absorbent body contents to leave the paper diaper, and the pulp fibers were dispersed into the liquid inside the washing tank. After using a strainer with a hole size of φ10 mm to sift out the large-sized solids from the nonwoven fabric and film that were floating in the liquid inside the washing tank, they were drained, and the pulp fibers and inactivated superabsorbent polymer remaining in the tank, as well as the pulp fibers and inactivated superabsorbent polymer that had been discharged out of the tank together with the drainage, were recovered and subjected to ATP inspection. The results of the ATP inspection yielded an ATP value of 0.

Although portions of the nonwoven fabric with the film attached were also present among the large solids sifted out with the strainer, the film could be easily and cleanly detached from the nonwoven fabric.

Next, the pulp fibers and inactivated superabsorbent polymer were placed in a nylon net (250 mesh nylon net by NBC Meshtec, Inc.) bag (250 mm×250 mm), and dewatered for 5 minutes in a dewatering tank. The dewatered pulp fibers and inactivated superabsorbent polymer were immersed in a 1.0 mass % sodium hypochlorite aqueous solution together with the nylon net bag and subjected to stirring and washing for 5 minutes, and after again dewatering for 5 minutes in a dewatering tank, they were dried for 24 hours with a hot air drier at 105° C., and then the pulp fibers were recovered. The ash content of the recovered pulp fibers was analyzed to be 0.28 mass %.

Example 2

This was carried out in the same manner as Example 1, except that the d-limonene concentration was changed to 0.1 mass %. After 15 minutes of washing, the front sheet and back sheet of the paper diaper in the washing tank were detached, causing the absorbent body contents to leave the paper diaper, and the pulp fibers were dispersed into the liquid inside the washing tank.

Comparative Example 1

This was carried out in the same manner as Example 1, except that the d-limonene concentration was changed to 0.01 mass %. After 15 minutes of washing, the front sheet and back sheet of the paper diaper in the washing tank were still attached, and the absorbent body was still held inside the paper diaper.

Comparative Example 2

This was carried out in the same manner as Example 1, except that the d-limonene concentration was changed to 0.03 mass %. After 15 minutes of washing, the front sheet and back sheet of the paper diaper in the washing tank were still attached, and the absorbent body was still held inside the paper diaper.

Comparative Example 3

A test was conducted by the method described in Japanese Unexamined Patent Publication No. 2010-84031. Specifically, after using commercially available paper diapers (Moony® M size, by Unicharm Corp.) to absorb 240 mL of the previously prepared artificial sewage, one paper diaper was loaded into a washing tank of a dual-tank miniature washing machine ("HareBare" AST-01 by Alumis Co.), 80 g of CaO (product of Wako Pure Chemical Industries, Ltd.) was further loaded into the washing tank, and then 6.5 L of a sodium hypochlorite aqueous solution at 250 ppm by mass (prepared by dilution of a product purchased from Wako Pure Chemical Industries, Ltd.) was loaded in. After 15 minutes of washing, the paper diaper floating in the liquid inside the washing tank was recovered, and since the diaper had retained its form without separation, the surface material was physically torn by hand to recover the pulp fibers including the inactivated superabsorbent polymer inside the diaper. The ash content of the recovered pulp fibers was analyzed to be 15.9 mass %.

Example 3

One commercially available paper diaper (Moony® M Size by Unicharm Corp.) was loaded into a washing tank of a dual-tank miniature washing machine ("HareBare" AST-01 by Alumis Co.). Next, 200 g of citric acid and 100 g of d-limonene were dissolved in 10 L of water and loaded into the washing tank. The washing machine was operated for 9 minutes of agitation. After agitation was complete, the front sheet and back sheet of the paper diaper were detached, causing the absorbent body contents to leave the paper diaper, and the pulp fibers were dispersed into the liquid inside the washing tank. The large solids from the nonwoven fabric and film floating in the liquid inside the washing tank were sifted out and recovered with a wire net having a 10 mm mesh opening. They were then drained, and the pulp fibers and inactivated superabsorbent polymer remaining in the washing tank, as well as the pulp fibers and inactivated superabsorbent polymer that had been discharged out of the tank together with the drainage, were recovered and subjected to ATP inspection.

FIG. 1 shows a photograph of the paper diaper before treatment, FIG. 2A shows a photograph of the washing tank interior after treatment, FIG. 2B shows a photograph of the recovered nonwoven fabric, film, etc. after treatment, and FIG. 2C shows a photograph of the recovered pulp fibers and inactivated superabsorbent polymer after treatment.

The paper diaper was cleanly disintegrated, and could be easily separated into the large solids such as the nonwoven fabric and film, and the pulp fibers and inactivated superabsorbent polymer.

Example 4

This was carried out in the same manner as Example 3, except that the d-limonene was changed to 3-carene.

FIG. 3A shows a photograph of the washing tank interior after treatment, FIG. 3B shows a photograph of the recovered nonwoven fabric, film, etc. after treatment, and FIG. 3C shows a photograph of the recovered pulp fibers and inactivated superabsorbent polymer after treatment.

The paper diaper was cleanly disintegrated, and could be easily separated into the large solids such as the nonwoven fabric and film, and the pulp fibers and inactivated superabsorbent polymer.

Example 5

This was carried out in the same manner as Example 3, except that the d-limonene was changed to a-pinene.

Figure 4B:
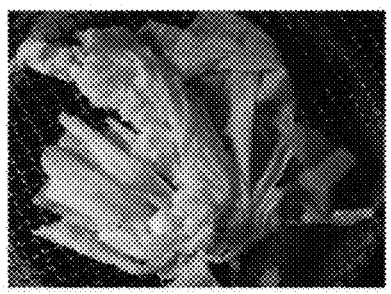
FIG. 4B shows a photograph of the recovered nonwoven fabric, film, etc. after treatment.
Figure 4C:
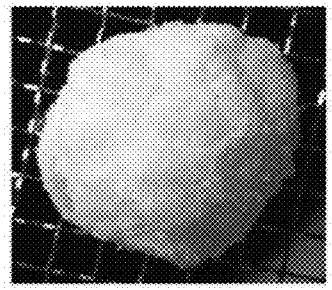
FIG. 4C shows a photograph of the recovered pulp fibers and inactivated superabsorbent polymer after treatment.

FIG. 4A shows a photograph of the washing tank interior after treatment, FIG. 4B shows a photograph of the recovered nonwoven fabric, film, etc. after treatment, and FIG. 4C shows a photograph of the recovered pulp fibers and inactivated superabsorbent polymer after treatment.

The paper diaper was cleanly disintegrated, and could be easily separated into the large solids such as the nonwoven fabric and film, and the pulp fibers and inactivated superabsorbent polymer.

Example 6

This was carried out in the same manner as Example 3, except that the 100 g of d-limonene was change to 89.4 g (100 mL) of citral.

Figure 5A:
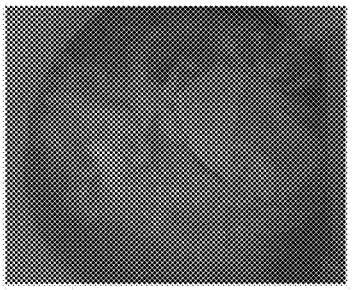
FIG. 5A shows a photograph of the washing tank interior after the treatment of Example 6.
Figure 5B:
FIG. 5B shows a photograph of the recovered nonwoven fabric, film, etc. after treatment.
Figure 5C:
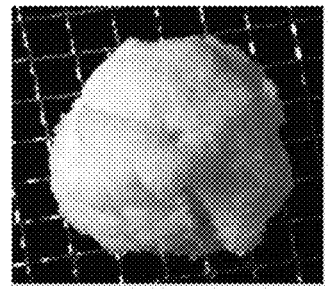
FIG. 5C shows a photograph of the recovered pulp fibers and inactivated superabsorbent polymer after treatment.

FIG. 5A shows a photograph of the washing tank interior after treatment, FIG. 5B shows a photograph of the recovered nonwoven fabric, film, etc. after treatment, and FIG. 5C shows a photograph of the recovered pulp fibers and inactivated superabsorbent polymer after treatment.

The paper diaper was cleanly disintegrated, and could be easily separated into the large solids such as the nonwoven fabric and film, and the pulp fibers and inactivated superabsorbent polymer.

Example 7

This was carried out in the same manner as Example 3, except that the 100 g of d-limonene was changed to 91.3 g (100 mL) of y-terpinene.

Figure 6A:
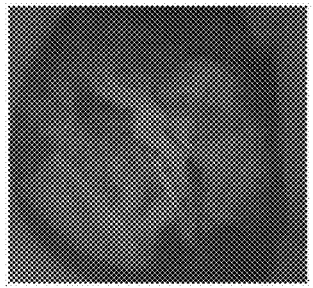
FIG. 6A shows a photograph of the washing tank interior after the treatment of Example 7.
Figure 6B:
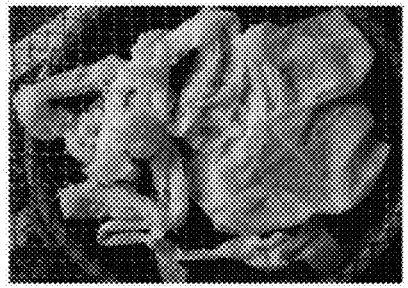
FIG. 6B shows a photograph of the recovered nonwoven fabric, film, etc. after treatment.
Figure 6C:
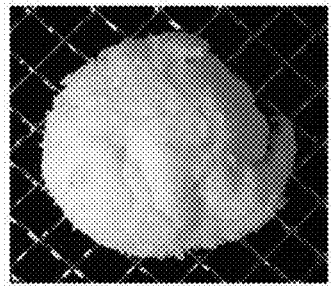
FIG. 6C shows a photograph of the recovered pulp fibers and inactivated superabsorbent polymer after treatment.

FIG. 6A shows a photograph of the washing tank interior after treatment, FIG. 6B shows a photograph of the recovered nonwoven fabric, film, etc. after treatment, and FIG. 6C shows a photograph of the recovered pulp fibers and inactivated superabsorbent polymer after treatment.

The paper diaper was cleanly disintegrated, and could be easily separated into the large solids such as the nonwoven fabric and film, and the pulp fibers and inactivated superabsorbent polymer.

The method of analyzing the ash content is as follows.

[Method of Analyzing Ash Content]

The ash content is the amount of inorganic substances or nonflammable residue remaining after the organic substances have been ashed. The ash content is measured according to the Sanitary Product Material Standards, "2. General test methods", "5. Ash content test method". Specifically, the ash content is measured in the following manner.

A platinum, quartz or magnetic crucible is strongly preheated at 500 to 550° C. for 1 hour, and after standing to cool, the mass is precisely measured. After taking 2 to 4 g of sample and placing it in the crucible, the mass is precisely measured, removing or displacing the cover of the crucible if necessary, and gentle heating is performed first, followed by gradual increase in the temperature to strong heating at 500 to 550° C. for 4 hours or longer, ashing it until no more carbides remain. After being allowed to cool, the mass is precisely measured. The residue is again ashed until reaching a constant mass, and after cooling, the mass is precisely measured and recorded as the ash content (mass %).

INDUSTRIAL APPLICABILITY

The method of the invention can be suitably utilized for recovering pulp fibers from a used absorbent article that contains pulp fibers and a superabsorbent polymer.

The invention claimed is:

1. A method of recovering pulp fibers from a used absorbent article that contains pulp fibers and a superabsorbent polymer, wherein the method includes a step of treating the used absorbent article with an aqueous solution containing at least one kind of terpene selected from the group consisting of terpene hydrocarbons, terpene aldehydes and terpene ketones at 0.05 mass % or greater, and also containing an inactivating agent that can inactivate the superabsorbent polymer, to inactivate the superabsorbent polymer.

2. The method according to claim 1, which further includes a step of separating the pulp fibers and the inactivated superabsorbent polymer from the used absorbent article that has been treated with the aqueous solution.

3. The method according to claim 2, which further includes a step of treating a mixture comprising the separated pulp fibers and the inactivated superabsorbent polymer with an oxidizing agent to decompose, reduce in molecular weight and solubilize the inactivated superabsorbent polymer.

4. The method according to claim 3, which further includes a step of separating the pulp fibers from the mixture that has been treated with the oxidizing agent.

5. The method according to claim 1, wherein the aqueous solution containing the inactivating agent that can inactivate the superabsorbent polymer is an organic acid aqueous solution with a pH of no higher than 2.5.

6. The method according to claim 5, wherein the organic acid is citric acid.

7. The method according to claim 6, wherein a citric acid concentration in the organic acid aqueous solution is 2 mass % or greater.

8. The method according to claim 1, wherein the terpene is a terpene hydrocarbon.

9. The method according to claim 8, wherein the terpene is at least one selected from the group consisting of limonene, carene, pinene, terpinene and citral.

10. The method according to claim 1, wherein a terpene concentration in the aqueous solution is 0.05 to 1.0 mass %.

11. The method according to claim 2, wherein the used absorbent article includes a material composed of a thermoplastic resin, and the method further includes a step of drying a residue obtained from separating the pulp fibers and the inactivated superabsorbent polymer from the used absorbent article, and separating the material composed of a thermoplastic resin from the dried residue.

12. The method according to claim 2, wherein the used absorbent article includes a thermoplastic resin film, and the method further includes a step of drying a residue obtained from separating the pulp fibers and the inactivated superabsorbent polymer from the used absorbent article, and separating the thermoplastic resin film from the dried residue.

13. The method according to claim 1, wherein the absorbent article is at least one type selected from the group consisting of paper diapers, urine-absorbing pads, bed sheets, sanitary napkins and pet sheets.

* * * * *